(12) United States Patent
Tian et al.

(10) Patent No.: US 10,345,246 B2
(45) Date of Patent: Jul. 9, 2019

(54) DARK FIELD WAFER NANO-DEFECT INSPECTION SYSTEM WITH A SINGULAR BEAM

(71) Applicant: Tokyo Electron Limited, Tokyo (JP)

(72) Inventors: Xinkang Tian, Fremont, CA (US); Ching-Ling Meng, Sunnyvale, CA (US); Yan Sun, Fremont, CA (US)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 15/611,290

(22) Filed: Jun. 1, 2017

(65) Prior Publication Data
US 2017/0350826 A1     Dec. 7, 2017

Related U.S. Application Data

(60) Provisional application No. 62/344,575, filed on Jun. 2, 2016.

(51) Int. Cl.
| | | |
|---|---|---|
| *G01N 21/88* | (2006.01) | |
| *G01N 21/49* | (2006.01) | |
| *G01N 21/95* | (2006.01) | |
| *G01N 21/47* | (2006.01) | |

(52) U.S. Cl.
CPC ......... *G01N 21/8806* (2013.01); *G01N 21/49* (2013.01); *G01N 21/9501* (2013.01); *G01N 2021/4735* (2013.01); *G01N 2021/8822* (2013.01); *G01N 2201/06113* (2013.01)

(58) Field of Classification Search
CPC ............... G01N 21/8806; G01N 21/49; G01N 21/9501; G01N 2201/06113; G01N 2021/4735; G01N 2021/8822
See application file for complete search history.

(56) References Cited

U.S. PATENT DOCUMENTS

| | | | |
|---|---|---|---|
| 4,893,932 A | 1/1990 | Knollenberg | |
| 5,781,294 A * | 7/1998 | Nakata | G01N 21/1702 356/487 |
| 6,288,780 B1 | 9/2001 | Fairley et al. | |
| 6,504,618 B2 * | 1/2003 | Morath | G01B 11/0666 356/630 |
| 7,006,221 B2 * | 2/2006 | Wolf | G01B 11/0666 356/369 |

(Continued)

FOREIGN PATENT DOCUMENTS

EP      0 935 772 B1    12/2002

OTHER PUBLICATIONS

International Search Report and Written Opinion dated Aug. 11, 2017 in PCT/US2017/035187.

(Continued)

*Primary Examiner* — Mohamed K Amara
(74) *Attorney, Agent, or Firm* — Oblon, McClelland, Maier & Neustadt, L.L.P.

(57) ABSTRACT

Provided is a method, system, and apparatus for inspecting a substrate. The method comprises illuminating the substrate with a singular laser beam, the singular laser beam forming an illuminated spot on the substrate and a bright fringe at a surface of the substrate, the bright fringe extending over at least a portion of the illuminated spot, and detecting, by an optical detection system, scattered light from nano-defects present on the substrate within the illuminated spot.

20 Claims, 7 Drawing Sheets

(56) References Cited

U.S. PATENT DOCUMENTS

| | | | |
|---|---|---|---|
| 7,554,655 B2* | 6/2009 | Fairley | G01N 21/8806 356/237.4 |
| 7,705,331 B1* | 4/2010 | Kirk | G01N 21/956 250/306 |
| 7,746,469 B2 | 6/2010 | Shamir et al. | |
| 8,912,495 B2* | 12/2014 | Lange | G01N 21/3563 250/338.1 |
| 9,194,811 B1* | 11/2015 | Zhao | G01N 21/9501 |
| 9,753,379 B2* | 9/2017 | Singh | G01J 3/2823 |
| 2002/0106848 A1* | 8/2002 | Wack | G01N 21/211 438/200 |
| 2002/0109848 A1* | 8/2002 | Hendriks | G01N 21/9501 356/484 |
| 2003/0020904 A1* | 1/2003 | Uto | G01N 21/21 356/237.2 |
| 2004/0207836 A1* | 10/2004 | Chhibber | G01N 21/4738 356/237.4 |
| 2005/0052642 A1* | 3/2005 | Shibata | G01N 21/8806 356/237.1 |
| 2005/0099633 A1 | 5/2005 | Failes | |
| 2005/0231713 A1* | 10/2005 | Owen | G01N 21/8806 356/237.1 |
| 2006/0215175 A1 | 9/2006 | Yacoubian | |
| 2007/0070336 A1* | 3/2007 | Maeda | G01N 21/8806 356/237.2 |
| 2009/0081512 A1* | 3/2009 | Blanchard | H01M 8/122 429/425 |
| 2009/0297725 A1 | 12/2009 | Reynoldson | |
| 2011/0231134 A1* | 9/2011 | Yoshitake | B82Y 10/00 702/94 |
| 2013/0003152 A1* | 1/2013 | Belousov | G01B 11/162 359/9 |
| 2013/0265572 A1* | 10/2013 | Delgado | G01N 21/8806 356/237.5 |
| 2015/0226676 A1 | 8/2015 | Nicolaides et al. | |
| 2017/0108444 A1* | 4/2017 | Otani | G01B 11/30 |
| 2017/0281102 A1* | 10/2017 | Ken | A61B 6/4258 |

OTHER PUBLICATIONS

A.s. van de Nes et al., "Rigorous Analysis of Spheres in Gauss-Laguerre Beams," Optics Express, Oct. 1, 2007, vol. 15, No. 20, 15 Pages.

Evyatar Hemo et al., "Scattering of Singular Beams by Subwavelength Objects," Applied Optics, Jan. 1, 2011, vol. 50, No. 1, pp. 33-42.

* cited by examiner

π phase jump

DARK FIELD WAFER NANO-DEFECT INSPECTION SYSTEM WITH A SINGULAR BEAM

CROSS REFERENCE TO RELATED APPLICATIONS

The present application claims the benefit of priority from U.S. Provisional Patent Application No. 62/344,575, entitled "DARK FIELD WAFER NANO-DEFECT INSPECTION SYSTEM WITH SINGULAR BEAMS" (Ref. No. TTI-245US1-PRO), filed on Jun. 2, 2016, the entire contents of which are incorporated herein by reference.

BACKGROUND OF THE INVENTION

The present disclosure relates to an optical wafer defect inspection system and associated methodologies. Optical wafer inspection methods can be roughly classified into two categories, bright-field methods and dark-field methods. Described herein is a dark-field method.

Optical detection of nano-defects on wafers is a very challenging issue. Researchers have been trying many different methods to increase a defect signal-to-noise ratio (SNR) and enhance throughput to make defects of a size less than 20 nm detectable on an inspection tool in a manufacturing setting. Those methods include using short wavelength light illumination, different polarization states, stronger light sources, different angle of incidences (AOI), the use of high-quality imaging subsystems, aperture shaping, the use of low noise sensors, and the like.

The foregoing "Background" description is for the purpose of generally presenting the context of the disclosure. Work of the inventor, to the extent it is described in this background section, as well as aspects of the description which may not otherwise qualify as prior art at the time of filing, are neither expressly or impliedly admitted as prior art against the present invention.

SUMMARY OF THE INVENTION

An aspect of the invention includes a method for inspecting a substrate comprising illuminating the substrate with a singular laser beam, the singular laser beam forming an illuminated spot on the substrate and a bright fringe at a surface of the substrate, the bright fringe extending over at least a portion of the illuminated spot; and detecting, by an optical detection system, scattered light from nano-defects present on the substrate within the illuminated spot.

Another aspect of the invention includes a system for inspecting a substrate. The system includes a substrate stage for receiving the substrate, a laser light source, illumination optics for directing light from the laser light source to a surface of the substrate, wherein the illumination optics are configured to form a singular laser beam for illuminating the substrate, and an optical detection system for detecting illuminated nano-defects by detecting scattered light from the illuminated nano-defects on the substrate.

Yet another aspect of the invention includes an apparatus for inspecting a substrate. The apparatus includes an illumination system for forming a singular laser beam from a laser light source and directing the singular laser beam to the substrate, and an optical detection system for detecting illuminated nano-defects by detecting scattered light from the illuminated nano-defects on the substrate.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Referring now to the drawings, wherein like reference numerals designate identical or corresponding parts throughout several views, the following description relates to an inspection system, sensor, and associated methodologies for substrate (i.e., wafer) inspection. The inspection system is a dark-field system where specular reflection light from the substrate is not collected and only the scattering light from defects are caught by a detector through an imaging path.

Reference throughout the specification to "one embodiment" or "an embodiment" means that a particular feature, structure, material, or characteristic described in connection with the embodiment is included in a least one embodiment, but do not denote that they are present in every embodiment. Thus the appearances of the phrases "in one embodiment" in various places through the specification are not necessarily referring to the same embodiment. Furthermore, the particular features, structures, materials, or characteristics may be combined in any suitable manner in one or more embodiments. It is noted that numbered reference numbers used within the description may refer to like numbered reference numbers appearing in one or more previous and/or subsequent drawings as liked numbered reference numbers are utilized herein to indicate similar items in the description and drawings.

Figure 1:
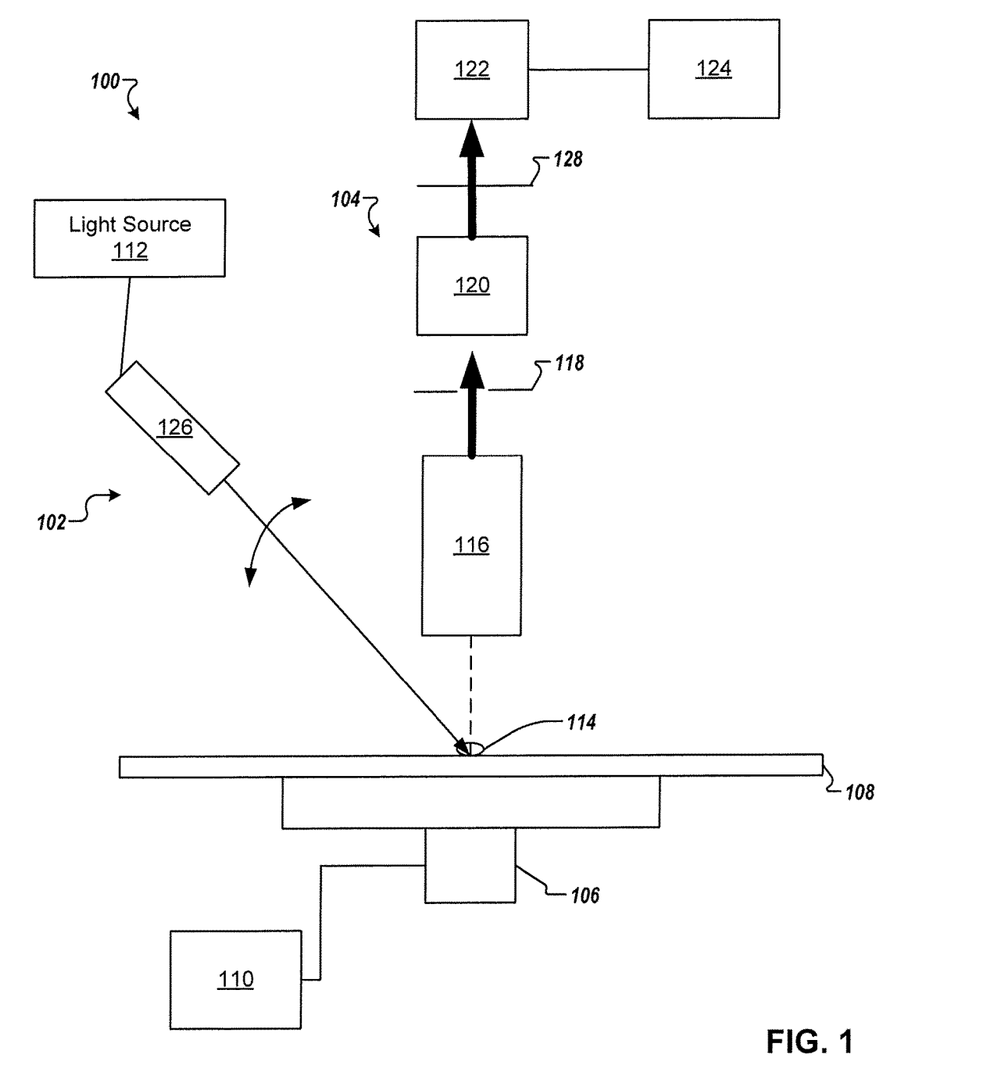
FIG. 1 is a side view schematic of an inspection system according to one example.

FIG. 1 is a side view schematic of an inspection system 100 according to one example. The inspection system 100 includes an illumination system 102 and an imaging system 104. The inspection system 100 includes a stage 106 configured to receive a substrate 108 (e.g., semiconductor wafer, integrated circuit). Substrate nano-defect inspection is done by scanning a field of view (FOV) of the imaging system 104 across the whole substrate through moving of the stage 106 and/or the whole optical system (i.e., the illumination system 102 and the imaging system 104). The stage 106 may include a chuck such as an electrostatic chuck, a vacuum chuck, for securing the substrate 108. The stage 106 may be a precision stage which may be controlled by a controller 110 to scan an incident beam across the whole substrate 108. In one implementation, the substrate 108 under inspection is held by a vacuum pin-chuck mounted on an air-bearing stage. The air-bearing stage allows movement of the substrate 108 to locate an illuminated spot on the substrate 108. The controller 110 may be a general purpose computer.

The illumination system 102 is configured to direct at least one singular laser beam to the substrate 108 at a variable angle of incidence (AOI). A singular beam is created based on a special mechanism from conventional laser sources as described later herein. The singular beam refers to a combination of Gauss-Laguerre beams or modified forms of Gauss-Laguerre beams. Illumination with the singular beam enhances a light signal scattered from nano-defects on a surface of the substrate 108 or embedded in the layers formed atop the substrate 108, as described further below. In addition, the singular beam provides higher illumination intensity over at least a portion of the substrate surface compared to a Gaussian beam for the same power.

The illumination system 102 may include a light source 112. The light source 112 may be one or more laser light sources that may have different wavelengths in one or more portions of the light spectrum such as extreme ultraviolet (EUV), deep ultra violet (DUV), ultra violet (UV), and visible. The wavelength of the singular laser beam is selectively switchable. The capability of switching/selecting the illumination wavelength among EUV, DUV, UV, and visible light wavelength ranges provides a way to avoid substrate layer damage caused by the exposure to DUV or UV light due to over-dosing of high-energy photons during inspection. In one implementation, the laser source may be a neodymium-doped yttrium aluminum garnet (Nd:YAG) laser having a wavelength of 266 nm (i.e., $4^{th}$ harmonic output) or a Nd:YAG having a wavelength of 355 nm (i.e., third harmonic output).

The singular laser beam has a linear polarization state, which can be rotated to construct s- or p-illumination at the surface of the substrate 108. In one implementation, the singular laser beam may have circular polarization. A switchable quarter-wave may be used to transform linear to circular polarization. The angle of incidence of the illumination beam is configurable based on application needs. The AOI can be changed from a near-normal incident angle to a grazing incident angle. In other words, the AOI and the polarization states are modified to maximize a signal noise ratio (SNR) based on a type of the substrate 108 being inspected. The AOI of the singular laser beam may be from about 1° to about 90°. In one implementation, the AOI of the singular laser beam is in the range of about 5° to about 85°. The illumination system 102 includes illumination optics 126. The illumination optics 126 may include one or more lenses configured to focus the singular beam on the substrate 108. An illumination spot size from the illumination optics 126 may range from 2 μm to 10 μm. The one or more lenses may have an effective focal length (EFL) of 50 mm. The illumination optics 126 may include a beam expander having a magnification ranging from 3.7× to 27.4×. In order to provide the adjustable angle for the illumination beam, the illumination system 102 may be positioned on a mechanical stage. Further, the illumination system 102 may include electro-optical modulators for tuning the angle of incidence.

In one implementation, the illumination system 102 is configured to create two illuminations paths from left and right of the center of the substrate 108, respectively. The beams in both paths may be identical.

Figure 10:
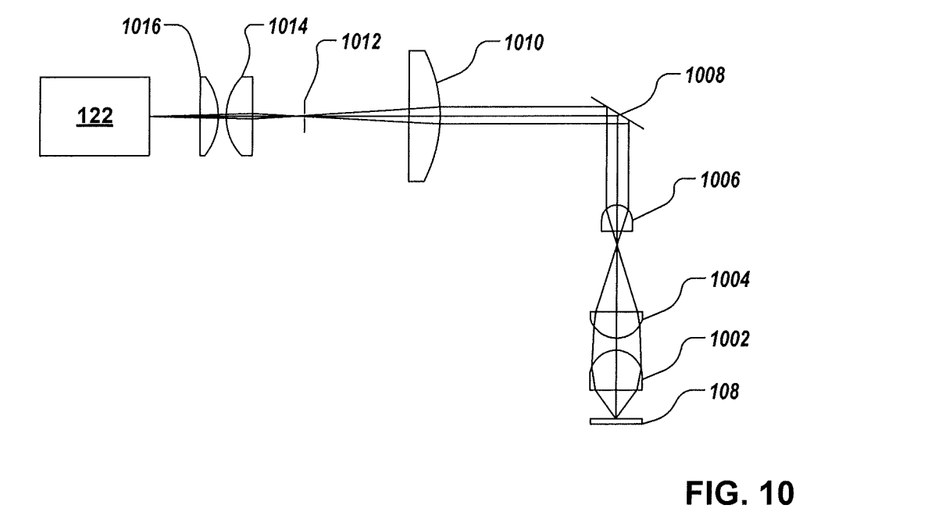
FIG. 10 is a schematic that shows an imaging system of the inspection system according to one example.
Figure 11:
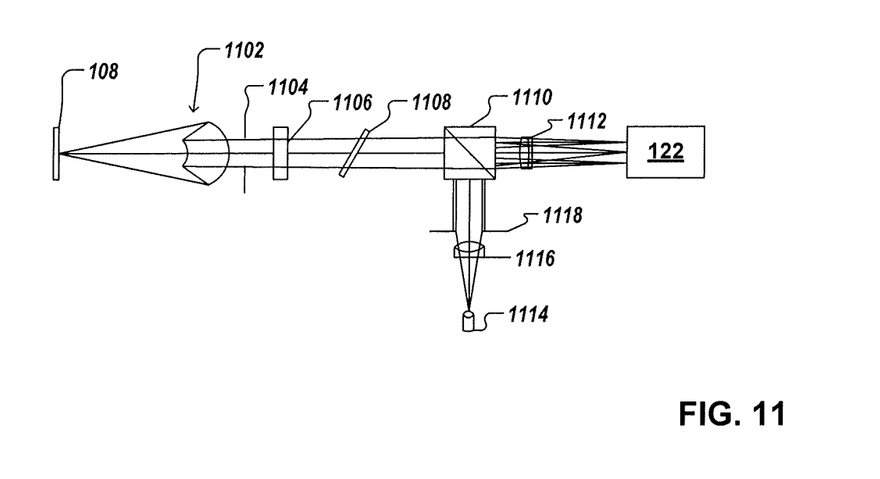
FIG. 11 is a schematic that shows an imaging system of the inspection system according to another example.

A precision imaging path is built perpendicular to the substrate surface using the imaging system 104. The imaging system 104 may include an objective lens 116, a configurable imaging aperture 118, relay optics 120, and a detector array 122. The objective lens 116 can be a reflection type without chromatic aberration or a transmission type with correction of chromatic aberration at multiple wavelengths. In one implementation, the objective lens 116 is optimized to minimize chromatic aberration at least two different wavelengths of light. The objective lens 116 is configured to detect light from detection area 114. The configurable imaging aperture 118 can take different shapes to maximize defect signal and block unwanted light from reaching the detector array 122. The relay optics 120 may include a group of lens, compensators, and bandpass filters (e.g., bandpass filter 128). The relay optics 120 is configured to modify magnification and correct residual aberrations to create a high-quality image at the detector array 122. The light wavelength passband of the bandpass filter 128 is selected to block interfering light emissions from the substrate 108. The bandpass filters help to keep fluorescence light from reaching the detector array 122. The imaging system 104 may include a high speed autofocus system for maintaining focus during detection of the scatter light from nano-defects on the substrate 108. In other words, the autofocus system keeps the area in the FOV of the imaging system 104 in focus during substrate scans. The imaging system 104 may have a large numerical aperture (NA). For example, the imaging system 104 may have a NA of 0.6. Exemplary embodiments of the imaging system are shown in FIGS. 10 and 11.

The detector array 122 with ultra-low noise and high-sensitivity to weak light signal is used in the inspection system 100 to increase overall system throughput. For example, a photomultiplier tube (PMT) array may be used. In one implementation, the detector array 122 may be a time delay integration (TDI) charged-couple device (CCD) array. The light signal is converted to photo-electronic signal at the detector array 122 and then be amplified. In one embodiment, a single detector array 122 may be used.

Next, the detected signal is sent to an image computer 124 for signal processing and determining whether a defect occurs within the field of view of the imaging system 104. The image computer 124 may process the acquired optical signal from the scattered light from the illuminated spot. The image computer 124 may be a general purpose computer.

In one implementation, the inspection system 100 may include a purge chamber for providing a controlled atmosphere for the substrate 108. For example, when a wavelength in the DUV range is used, the purge chamber may be purged with nitrogen to protect the substrate 108.

The detection sensitivity of a nanoparticle (or other nano-defect) in the inspection system 100 is directly related to the intensity of scattered light by the particle (or defect). Since the particle (or defect) is much smaller than light wavelength, the intensity of scattered light can be calculated according to Rayleigh scattering theory. The intensity of scattered light may be expressed as $$I_s \propto \frac{I}{\lambda^4}, \quad (1)$$

where I is the intensity of illumination light onto the defect, and $\lambda$ is the wavelength of light.

Figure 2A:
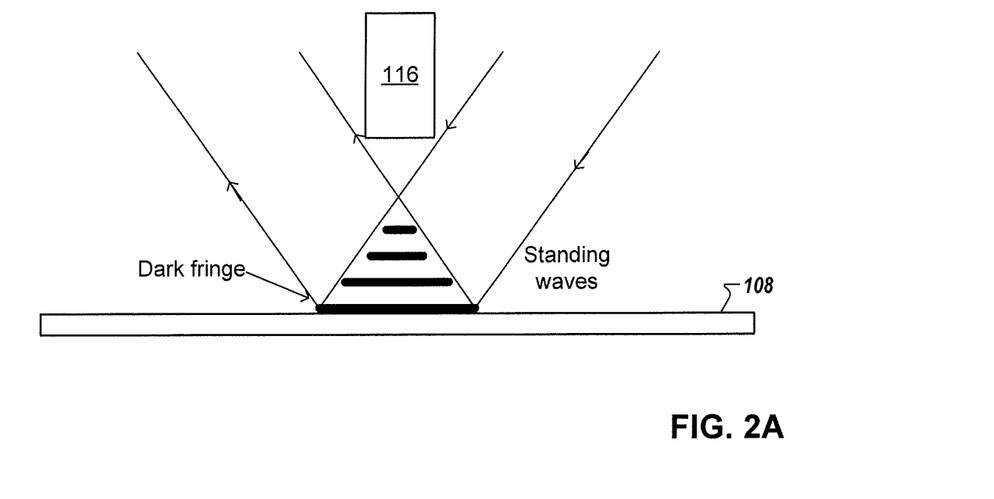
FIG. 2A is a schematic that shows standing waves generated by a collimated Gaussian beam according to one example.

When a collimated laser beam illuminates a surface of the substrate 108 at an oblique angle of incidence, standing waves are generated above the surface of the substrate 108 due to overlapping wave fronts of direct illumination and reflection from the substrate 108. If the illumination is using collimated Gaussian beams, the resultant standing waves have the profile as shown in FIG. 2A, where constructive interference (bright fringes) and destructive interference (dark fringes) occur within a triangular region between the substrate 108 and the objective lens 116. Due to the phase shift at the surface of the substrate 108, the standing waves have dark fringes locked at the surface of the substrate 108.

A fringe zone represents a standing wave pattern which is phase-locked to the surface of the substrate 108. For s-polarization there is a 180° phase shift, upon reflection thus the surface of the substrate 108 is generally in the first dark zone. The fringe spacing may be calculated using:

$$h = \lambda/2 \cos(\theta) \quad (2)$$

where h is the fringe spacing, $\theta$ is the angle of incidence, $\lambda$ is the wavelength of the illumination beam. The amplitude of the surface standing wave may be expressed as:

$$I(x,\theta) = I_t \sin((2\pi/\lambda)x) \cos\theta \quad (3)$$

where x is the distance from the surface of the substrate, and $I_t = 4I_i$.

Figure 2B:
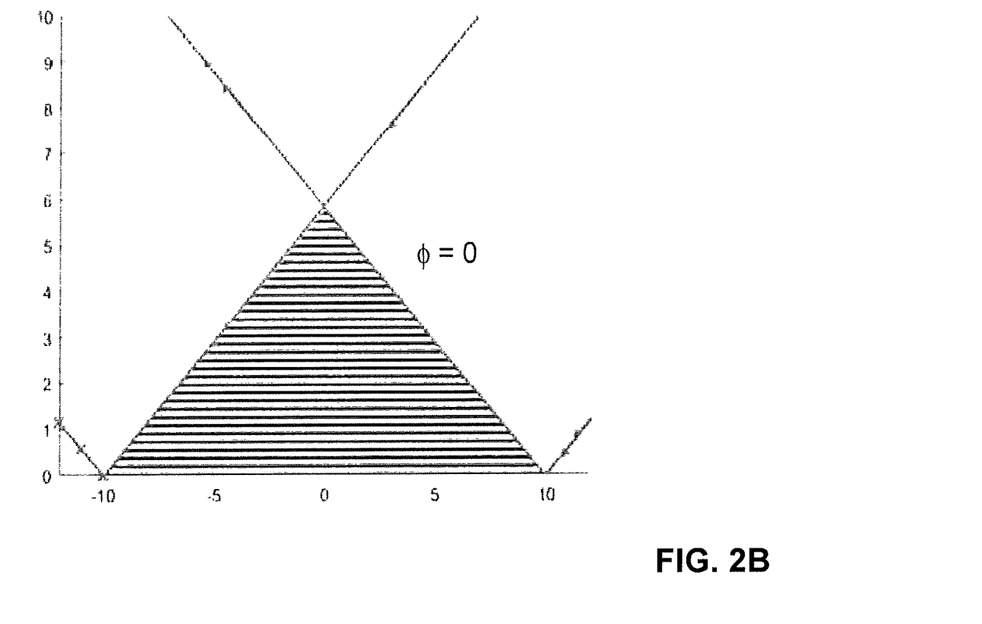
FIG. 2B is a schematic that shows standing waves generated by a 355 nm collimated Gaussian beam according to one example.
Figure 3:
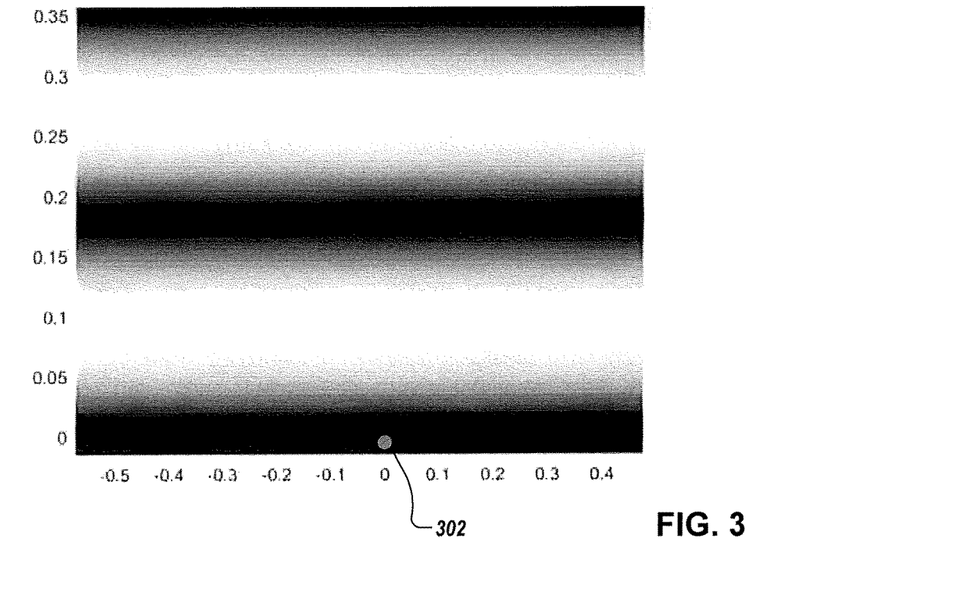
FIG. 3 is a schematic that shows a nanoparticle located in a dark fringe according to one example.

FIG. 2B illustrates a standing wave above the substrate surface generated by a 355 nm collimated Gaussian beam having a flat wavefront. FIG. 3 illustrates a magnified view of the standing waves near the substrate 108. The light intensity at the substrate surface is very weak (i.e., close to zero). If a nanoparticle 302 (or defect) is positioned on the substrate surface, the light illuminated on the nanoparticle 302 is very weak and thus the scattered light from the nanoparticle 302 is low. The x and y axis in FIG. 2A and FIG. 3 are in µm.

If a defect is located inside the triangular region and the defect is large (i.e., tall) enough to interact with bright fringes, the scattered light by the defect is more likely to be caught by the detector array 122 through the imaging path. In other words, when a defect is present within the region of standing waves and at least a part of the defect is exposed to the bright fringes, the scattered light from the defect is stronger than for defects sitting in the dark fringes. When the stronger scattered light is collected by the imaging system 104 and the low noise array detector 122, a defect signal with higher SNR can be generated. Changes of AOI and polarization states can re-shape the pitch and/or contrast of the standing waves so that a maximized defect signal is collected in the inspection system 100, and better overall defect sensitivity is achieved. The detector array 122 generates photocurrent called defect signal. If the defect signal is stronger than background noise (e.g., electrical noise of the system), then the defect signal is considered detectable.

However, the dimensions of most nano-defects are small. The nano-defects are just several nanometers above the surface of the substrate 108 and are generally located within the dark fringe where illumination intensity of the nanoparticle 302 is close to zero as illustrated in FIG. 3. In addition, the scattering cross section of nano-defects is generally very small. Adding those two factors together, the resultant defect signal is usually extremely weak and cannot beat the background noise. This is why detection of nano-defects is very difficult.

Figure 4:
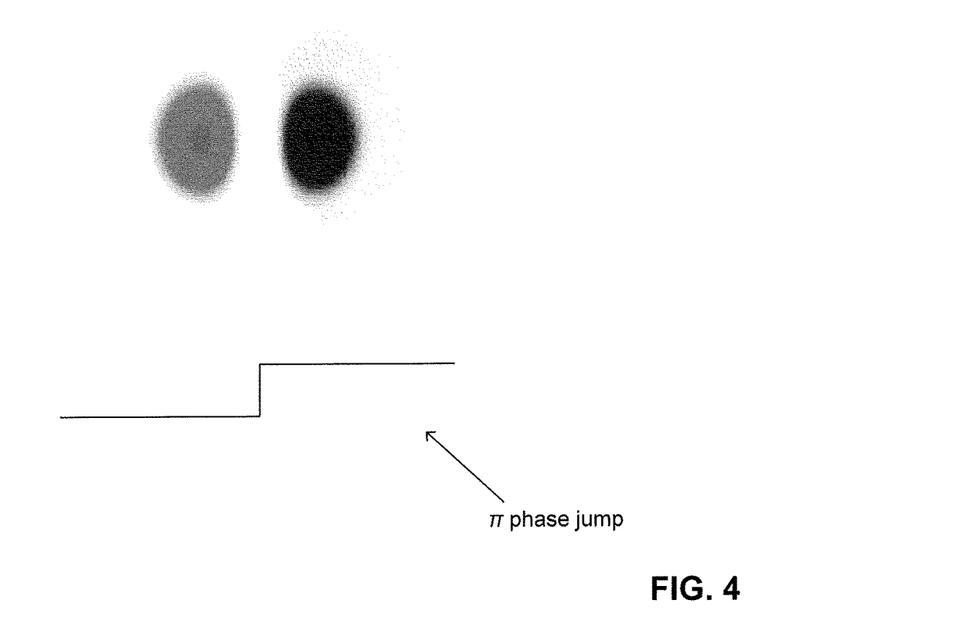
FIG. 4 is a schematic that shows a phase jump in a singular beam according to one example.
Figure 5A:
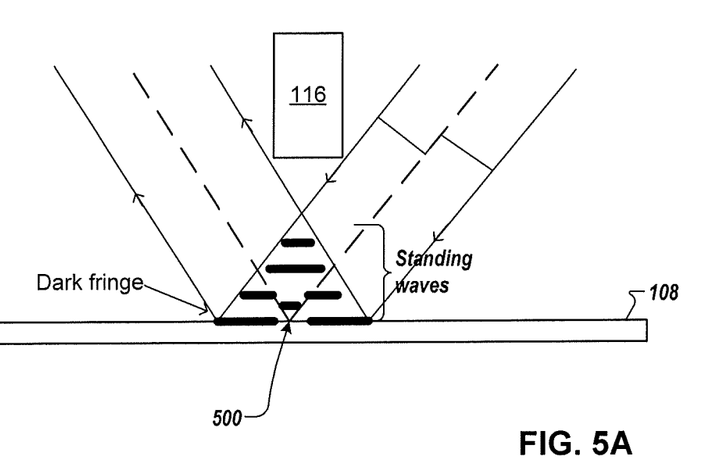
FIG. 5A is a schematic that shows standing waves generated by a collimated singular beam according to one example.
Figure 7:
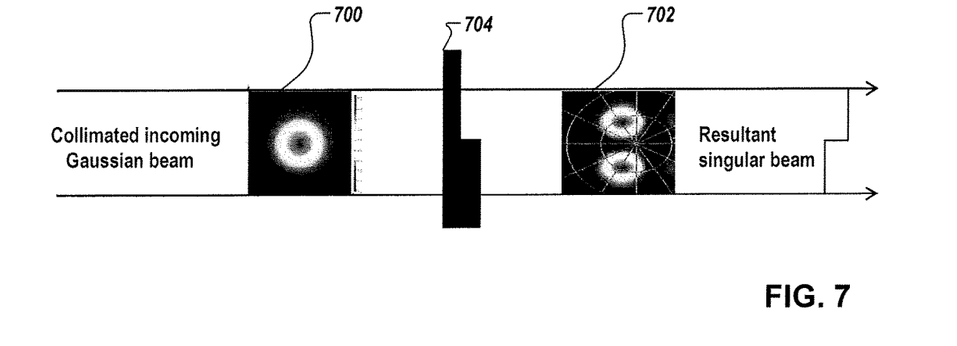
FIG. 7 is a schematic that shows how a collimated singular laser beam is generated from a collimated Gaussian beam according to one example.

To improve the detection sensitivity of nano-defects on the surface of the substrate 108, the inspection system 100 described herein uses singular laser beam illumination. The singular laser beam has at least two beam portions separated by a phase difference. The phase difference may be $\pi$ radians. FIG. 4 shows one example of a singular beam where a $\pi$ phase jump occurred along a center line of the beam cross section. The phase difference of the singular laser beam portions is formed using a phase mask or a phase retarder. An exemplary embodiment of a singular laser beam generation is shown in FIG. 7. When a singular illumination beam hits on the surface of the substrate 108, the illumination beam generates unique standing waves between the substrate 108 and objective lens 116, as shown in FIG. 5A. In the figures, the singular illumination beam is represented by two parallel solid lines with an arrow towards the substrate. The center-dotted line between the two parallels solid lines represents the center of the singular illumination beam.

Figure 5B:
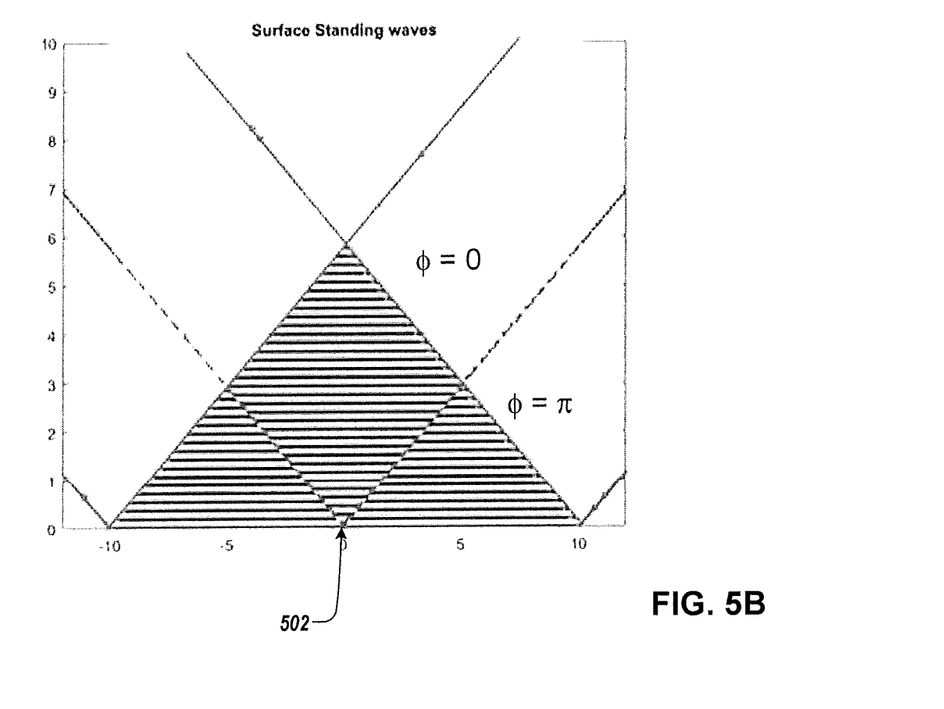
FIG. 5B is a schematic that shows standing waves generated by a 355 nm collimated singular beam according to one example.

A part of the standing waves has a bright fringe 500 locked at the surface of the substrate 108. The bright fringe 500 extends over at least a portion of an illuminated spot from the singular illumination beam. When a nano-defect interacts with the bright fringe 500, i.e., stronger illumination, the scattered light signal from the nano-defect may be several times higher than those sitting in a dark fringe (e.g., using Gaussian illumination), as described further below. This mechanism helps overall signal to noise ratio improvement for nano-defect inspection. For an incident singular beam, there are two adjacent beams with opposite phase. The standing wave pattern is flipped, where at the center of the incident beam, a constructive interference occurs and the fringe spacing can be expressed as h=$\lambda$/2 cos ($\theta$). As a result, a bright fringe zone 502 is formed as shown in FIG. 5B for a 355 nm collimated singular incident beam. The x-axis in FIG. 5B represents the horizontal distance in microns. The y-axis represents the distance from the substrate in microns. The resultant standing wave can be expressed as:

$$I(x,\theta) = I_t \cos((2\pi/\lambda)x) \cos\theta \quad (4)$$

Figure 6:
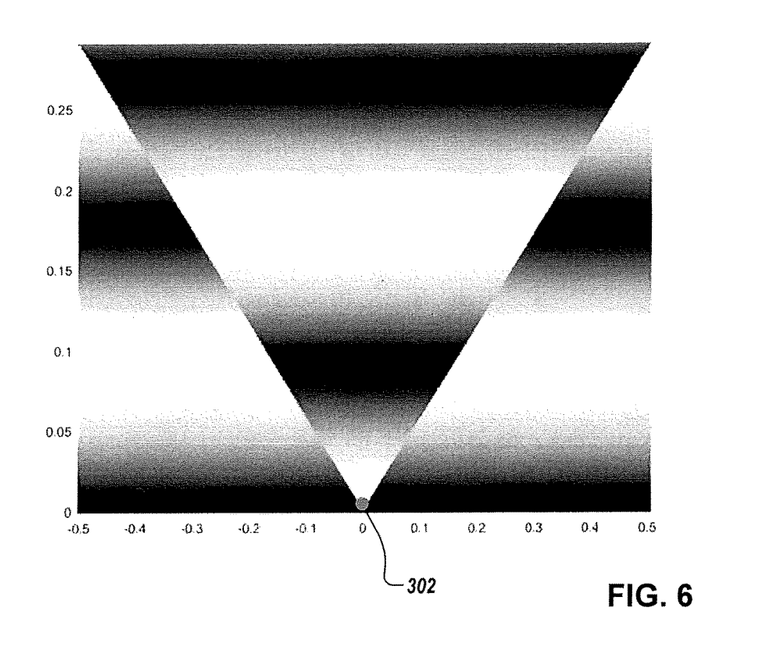
FIG. 6 is a schematic that shows the nanoparticle located in a bright fringe according to one example.

FIG. 6 illustrates a magnified view of the standing waves near the substrate 108 due to the collimated singular beam. If the nanoparticle 302 is located on the bright fringe as shown in FIG. 6, the light intensity illuminated onto the nanoparticle 302 can be 3-4 times the intensity of the Gaussian beam as shown further below. Due to the intensified illumination on the nanoparticle 302, a stronger scattered signal may be detected using the imaging system 104 (e.g., by applying equation (3)). The x-axis represents the horizontal distance in microns. The y-axis represents the distance from the substrate in microns.

The illumination intensity ratio between singular and Gaussian beam at an incident angle $\theta$ can be expressed as:

$$I_{singular}/I_{Gaussian} = [I_t \cos((2\pi/\lambda)x)\cos\theta]/[I_t \sin((2\pi/\lambda)x)\cos\theta] = \cot((2\pi/\lambda)x) \quad (5)$$

where x is the distance above the surface of the substrate. Thus, $$I_{singular}/I_{Gaussian} < 1 \text{ for } x > \lambda/8$$

$$I_{singular}/I_{Gaussian} = 1 \text{ for } x = \lambda/8$$

$$I_{singular}/I_{Gaussian} > 1 \text{ for } x < \lambda/8$$

As an example, for a 17 nm nanoparticle sitting above the substrate surface and illuminated by a collimated 355 nm laser beam, the singular beam creates three times of light intensity as that of a Gaussian beam (i.e., the collimated 355 nm laser beam without modification) on the particle surface (i.e., using equation (5)).

By optimizing the angle of incidence, state of polarization, and shape of imaging aperture, nano-defects on top of many different substrate layers or embedded in the previous layers are detected by the method described herein. In particular, the inspection system 100 and associated methodologies can detect nodes ranging from 20 nm to 5 nm.

There are many different ways to generate the singular laser beam. To get a uniform intensity distribution within the illuminated area, a beam shaping process is employed to create a flat top laser beam first, and then send it through a phase mask with a π phase jump at the center line.

Figure 8:
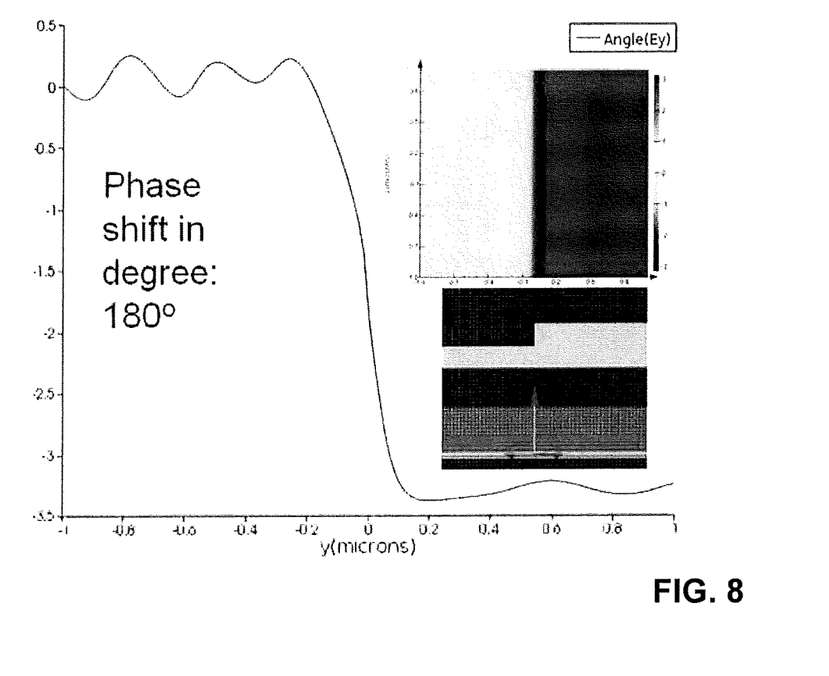
FIG. 8 is a schematic that shows a phase of the collimated singular laser beam according to one example.

The singular laser beam with one or more phase jumps can be created by inserting a specially designed phased mask into a regular Gaussian laser beam. FIG. 7 shows a Gaussian beam passing through a phase plate 704. The phase plate 704 has a step height of d=λ/2(n−1) where λ is the wavelength of the illumination light and n is the index of refraction. Schematic 700 shows the beam profile before passing through the phase plate 704. Schematic 702 shows the beam profile after passing through the phase plate 704 (i.e., beam profile of the singular beam). FIG. 8 shows the phase of the singular beam. The singular beam has a phase shift of about 180°. The x-axis in FIG. 8 is in microns. The x-axis represents a direction perpendicular to the direction of the incident beam. The y-axis in FIG. 8 is in radians.

Figure 9:
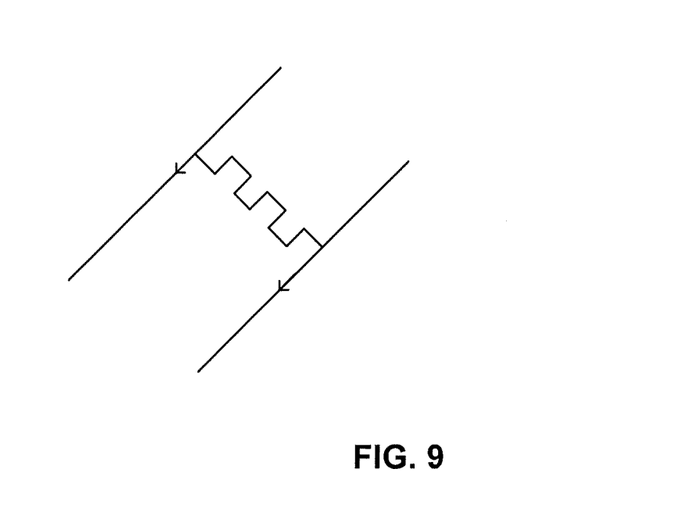
FIG. 9 is a schematic that shows a singular beam with multiple phase jumps according to one example.

FIG. 4 shows a singular illumination beam with one phase jump of π. In one implementation, a singular illumination beam can be created with multiple phase jumps across the cross-section of a beam, as shown in FIG. 9. The singular illumination beam with multiple phase jumps can be generated by inserting a specially designed phase mask into a regular Gaussian laser beam. Using the singular illumination beam with multiple phase jumps, a standing wave with multiple sections of bright fringes on the surface of the substrate 108 is generated. If a nanoparticle (or defect) located on the substrate surface is scanned through such a standing wave and the scattered signal is integrated at the detector 122 over a period of time, the particle detection sensitivity can be further improved compared with the case of one phase jump.

FIG. 10 is a schematic that shows the imaging system 104 according to one embodiment. In one implementation, the objective lens 116 may use refractive optics. The objective lens 116 has the task of collecting reflective light (referred to herein as collected light beam) from the detection area 114, so the collected light beam can be transmitted to the detector array 122 as described previously herein. The objective lens 116 may include a first lens 1002, a second lens 1004, and a third lens 1006. The first lens 1002 and the second lens 1004 are configured to expand the collected light beam. Lenses 1002, 1004, and 1006 may be aspheric lenses configured to reduce spherical aberrations. Then, the collected light beam may be passed through a dichroic filter/mirror 1008 configured to reflect light having a wavelength corresponding to the wavelength of the light source 112 (e.g., 266 nm or 355 nm). Then, a coupling lens 1010 serves to focus the light into pinhole 1012. Two coupling lenses 1014 and 1016 serve to focus the collected beam into the array detector 122. In one implementation, lenses 1010, 1014, and 1016 may be plano-convex lenses.

In one implementation, the objective lens 116 may be a reflective objective 1102 (e.g., two mirrors) as shown in FIG. 11. The collected light beam may be then passed through an aperture 1104 configured to limit the diameter of the collected light beam. The reflective objective 1102 may have a shoulder 1106 distance to the substrate ranging from 1 mm to 100 mm. For example, the distance may be 76.8 mm. Then, the collected light beam is passed through a dichroic filter 1108. The collected light beam is then passed through a beam splitter 1110 and a tube lens 1112. The tube lens 1112 is configured to focus the collect light beam into the detector 122. Additional light sources such as a white light emitting diode (LED) 1114 may be used for substrate alignment. The LED light is passed through a second aperture 1118 and through lens 1116.

For better performance in the UV part of the spectrum, i.e. 355 nm and less, UV-grade materials such as quartz, fused silica, CaF2 are used for all optical components.

Next, referring to FIG. 1, a hardware description of the image computer 124 according to exemplary embodiments is described. The image computer 124 may also perform functions and processes of the controller 110. The image computer 124 includes a multiple-core CPU which conducts parallel data processing described herein and the process data and instructions may be stored in memory. These processes and instructions may also be stored on a storage medium disk such as a hard drive (HDD) or a solid state drive or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the controller communicates, such as a server or computer.

Further, the claimed advancements may be provided as a utility application, background daemon, or component of an operating system, or combination thereof, executing in conjunction with CPU and an operating system such as Microsoft Windows, UNIX, Solaris, LINUX, Apple MAC-OS and other systems known to those skilled in the art.

In order to achieve the image computer 124, the hardware elements may be realized by various circuitry elements, known to those skilled in the art. For example, CPU may be a Xenon or Core processor from Intel of America or an Opteron processor from AMD of America, or may be other processor types that would be recognized by one of ordinary skill in the art. Alternatively, the CPU may be implemented on an FPGA, ASIC, PLD or using discrete logic circuits, as one of ordinary skill in the art would recognize. Further, CPU may be implemented as multiple processors cooperatively working in parallel to perform the instructions of the inventive processes described above.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

What is claimed is:

1. A method for inspecting a substrate, comprising:
   illuminating the substrate with a laser beam having a spatial phase singularity forming an illuminated spot on the substrate and a standing wave, the standing wave having at least one bright fringe and at least one dark fringe on the substrate, the at least one bright fringe extending over at least a portion of the illuminated spot; and
   detecting, by a dark field optical detection system, scattered light from nano-defects present on the substrate within the illuminated spot.

2. The method of claim 1, wherein the laser beam has at least two beam portions separated by a phase difference.

3. The method of claim 2, wherein the phase difference is π radians.

4. The method of claim 2, wherein the phase difference of the laser beam is formed using a phase mask or a phase retarder.

5. The method of claim 1, wherein the laser beam has an s polarization orientation at the substrate or a p polarization orientation at the substrate.

6. The method of claim 1, wherein an angle of incidence of the singular laser beam at the substrate is from about 1° to about 90°.

7. The method of claim 1, wherein the laser beam includes a light wavelength in the extreme ultraviolet (EUV), deep ultraviolet (DUV), ultraviolet (UV), or visible portions of the light spectrum, or a combination of two or more thereof.

8. The method of claim 1, wherein the dark field optical detection system is configured to detect scattered light from the nano-defects in a direction substantially perpendicular to the substrate.

9. The method of claim 1, wherein the dark field optical detection system comprises:
   an objective lens;
   a configurable imaging aperture;
   relay optics;
   a bandpass filter; and
   a detector array.

10. The method of claim 9, wherein the detector array comprises a photomultiplier tube (PMT) array or a time delay integration charge-coupled device (TDI CCD) array.

11. The method of claim 9, wherein the objective lens is optimized to minimize chromatic aberrations.

12. The method of claim 9, wherein the dark field optical detection system further comprises:
   an autofocus system for maintaining focus during detection of scattered light from nano-defects on the substrate.

13. The method of claim 9, wherein the dark field optical detection system further comprises:
   an image computer for signal processing an acquired optical signal from scattered light from illuminated nano-defects and for determining if a nano-defect occurs within the field of view of the dark field optical detection system.

14. The method of claim 1, wherein the nano-defects include defects located atop the substrate and all layers formed on the substrate.

15. A system for inspection a substrate, comprising:
   a substrate stage for receiving the substrate;
   a laser light source;
   illumination optics for directing light from the laser light source on the substrate, wherein the illumination optics are configured to form a laser beam having a spatial phase singularity for forming an illuminated spot on the substrate and a standing wave having at least one bright fringe and at least one dark fringe on the substrate; and
   a dark field optical detection system for detecting illuminated nano-defects by detecting scattered light from the illuminated nano-defects on the substrate.

16. The system of claim 15, further comprising:
   a purge chamber, wherein the substrate stage is deposited in the purge chamber.

17. The system of claim 15, wherein the dark field optical detection system comprises:
   an objective lens;
   a configurable imaging aperture;
   relay optics;
   a bandpass filter and
   a detector array.

18. The system of claim 17, wherein the detector array includes a photomultiplier tube (PMT) array or a time delay integration charge-coupled device (TDI CCD) array.

19. The system of claim 17, wherein the dark field optical detection system further comprises:
   an autofocus system for maintaining focus during detection of scattered light from nano-defects on the substrate.

20. An apparatus for inspecting a substrate, comprising:
   an illumination system for forming a laser beam having a spatial phase singularity from a laser light source and directing the laser beam to the substrate, the laser beam forming an illuminated spot and a standing wave having at least one bright fringe and at least one dark fringe on the substrate; and
   a dark field optical detection system for detecting illuminated nano-defects by detecting scattered light from the illuminated nano-defects on the substrate.

* * * * *

UNITED STATES PATENT AND TRADEMARK OFFICE
CERTIFICATE OF CORRECTION

PATENT NO. : 10,345,246 B2
APPLICATION NO. : 15/611290
DATED : July 9, 2019
INVENTOR(S) : Xinkang Tian et al.

It is certified that error appears in the above-identified patent and that said Letters Patent is hereby corrected as shown below:

In the Specification

In Column 6, Line 51, after "cos θ" insert -- . --.

In Column 7, Line 8, after "x<λ/8" insert -- . --.

In the Claims

In Column 9, Line 35, Claim 6, before "laser" delete "singular".

Signed and Sealed this
Twenty-first Day of April, 2020

Andrei Iancu
*Director of the United States Patent and Trademark Office*